United States Patent [19]
Gehrich et al.

[11] Patent Number: 5,462,052
[45] Date of Patent: Oct. 31, 1995

[54] APPARATUS AND METHOD FOR USE IN MEASURING A COMPOSITIONAL PARAMETER OF BLOOD

[75] Inventors: John L. Gehrich, Laguna Beach; Thomas P. Maxwell, Santa Ana; Thomas G. Hacker, Anaheim; Mark Z. Holody, Irvine, all of Calif.

[73] Assignee: Minnesota Mining And Manufacturing Co., St. Paul, Minn.

[21] Appl. No.: 55,800

[22] Filed: Apr. 27, 1993

Related U.S. Application Data

[63] Continuation of Ser. No. 564,800, Aug. 7, 1990, abandoned, which is a continuation-in-part of Ser. No. 229,617, Aug. 8, 1988, Pat. No. 4,989,606, which is a continuation-in-part of Ser. No. 8,937, Jan. 30, 1987, Pat. No. 4,830,013.

[51] Int. Cl.$^6$ ............................................. A61B 5/00
[52] U.S. Cl. .................. 128/632; 128/633; 128/665; 604/4; 422/82.04; 422/82.05
[58] Field of Search ............... 422/58, 68.1, 81, 422/82.04–82.11, 82.05; 436/56, 68, 138, 163; 128/632, 633, 636, 637, 665; 604/4–6

[56] References Cited

U.S. PATENT DOCUMENTS

| | | |
|---|---|---|
| Re. 31,879 | 5/1985 | Lubbers et al. . |
| 2,629,399 | 2/1953 | Kulick . |
| 3,335,715 | 8/1967 | Hugenholtz et al. ............... 128/2 |
| 3,433,935 | 3/1969 | Sherman . |
| 3,461,856 | 8/1969 | Polanyi . |
| 3,498,286 | 3/1970 | Polanyi et al. . |
| 3,512,517 | 5/1970 | Kadish et al. . |
| 3,529,591 | 9/1970 | Schuette . |
| 3,612,866 | 10/1971 | Stevens . |
| 3,616,409 | 10/1971 | Tosteson . |
| 3,658,053 | 4/1972 | Fergusson et al. . |
| 3,674,013 | 7/1972 | Polanyl . |
| 3,725,658 | 4/1973 | Stanley et al. ............... 250/71 R |
| 3,807,390 | 4/1974 | Ostrowski et al. . |
| 3,814,081 | 6/1974 | Mori . |
| 3,822,695 | 7/1974 | Takayama ............... 728/2 L |
| 3,841,308 | 10/1974 | Tate . |
| 3,865,548 | 2/1975 | Padawer ............... 23/230 R |
| 3,866,599 | 2/1975 | Johnson . |
| 3,878,830 | 4/1975 | Bicher . |
| 3,893,448 | 7/1975 | Brantigan . |
| 3,904,373 | 9/1975 | Harper ............... 23/253 TP |
| 3,983,864 | 10/1976 | Sielaff et al. . |
| 4,008,717 | 2/1977 | Kowarski . |

(List continued on next page.)

FOREIGN PATENT DOCUMENTS

| | | | |
|---|---|---|---|
| 0105870 | 4/1984 | European Pat. Off. | ....... G01N 33/84 |
| 0276977 | 8/1988 | European Pat. Off. | ......... A61B 5/00 |
| 2215984 | 10/1972 | Germany . | |
| 1593270 | 7/1981 | United Kingdom . | |
| 2132348 | 7/1984 | United Kingdom | ........... G01N 35/52 |
| WO84/01109 | 3/1984 | WIPO | ............ A61M 5/00 |

OTHER PUBLICATIONS

New Riverside University Dictionary, Houghton Mifflin Company, 1984, p. 474.
IEEE Transactions On Biomedical Engineering, vol. BME–33, No. 2, "Optical Fluorescence and Its Application to an Intravascular Blood Gas Monitoring System", pp. 117–132, IEE, New York, J. L. Gehrich et al. (Feb. 1986).

Primary Examiner—David A. Redding
Attorney, Agent, or Firm—Gordon L. Peterson

[57] ABSTRACT

A sensor cassette for use in measuring a compositional parameter of blood comprising a housing having a wall defining a passage which is adapted to receive blood. The wall is at least somewhat permeable to the compositional parameter. A support element, which is less permeable to the compositional parameter of blood than the housing, is carried by a region of the wall. A sensor is carried by the support element and provides a signal in response to the compositional parameter. The support element separates the sensor from at least a portion of such region of the wall so that the affect of the permeability of the housing to the compositional parameter on the signal from the sensor is reduced.

20 Claims, 4 Drawing Sheets

U.S. PATENT DOCUMENTS

| | | |
|---|---|---|
| 4,016,864 | 4/1977 | Sielaff et al. . |
| 4,050,450 | 9/1977 | Polanyi . |
| 4,073,297 | 2/1978 | Kopp . |
| 4,187,856 | 2/1980 | Hall et al. . |
| 4,194,877 | 3/1980 | Peterson ................................. 8/4 |
| 4,200,110 | 4/1980 | Peterson et al. . |
| 4,201,222 | 5/1980 | Haase . |
| 4,210,029 | 7/1980 | Porter . |
| 4,265,249 | 5/1981 | Schindler et al. . |
| 4,274,417 | 6/1981 | Delpy . |
| 4,282,881 | 8/1981 | Todd et al. ......................... 128/624 |
| 4,295,470 | 10/1981 | Shaw et al. . |
| 4,311,137 | 1/1982 | Gerard . |
| 4,322,164 | 3/1982 | Shaw et al. . |
| 4,340,615 | 7/1982 | Goodwin et al. . |
| 4,398,542 | 8/1983 | Cunningham et al. . |
| 4,399,099 | 8/1983 | Buckles ............................... 422/58 |
| 4,407,290 | 10/1983 | Wilber . |
| 4,471,765 | 9/1984 | Strauss . |
| 4,476,870 | 10/1984 | Peterson et al. . |
| 4,476,877 | 10/1984 | Barker . |
| 4,478,222 | 10/1984 | Koning et al. . |
| 4,487,206 | 12/1984 | Aagard ............................. 128/667 |
| 4,502,488 | 3/1985 | Degironimo et al. . |
| 4,508,123 | 4/1985 | Wyatt et al. . |
| 4,509,522 | 4/1985 | Manuccia et al. ................. 128/634 |
| 4,535,786 | 8/1985 | Kater . |
| 4,543,961 | 10/1985 | Brown . |
| 4,548,907 | 10/1985 | Seitz ................................. 436/163 |
| 4,557,900 | 12/1985 | Heitzmann . |
| 4,560,248 | 12/1985 | Cramp et al. ..................... 350/96.34 |
| 4,573,968 | 3/1986 | Parker . |
| 4,577,109 | 3/1986 | Hirschfeld ......................... 280/461.1 |
| 4,585,007 | 3/1986 | Uchigaki et al. . |
| 4,587,101 | 5/1986 | Marsoner et al. ................. 422/56 |
| 4,601,706 | 7/1986 | Aillon . |
| 4,608,996 | 9/1986 | Brown . |
| 4,640,820 | 2/1987 | Cooper . |
| 4,651,741 | 3/1987 | Passafaro . |
| 4,657,736 | 4/1987 | Marsoner et al. ................. 422/56 |
| 4,684,245 | 8/1987 | Goldring . |
| 4,718,423 | 9/1986 | Willis et al. . |
| 4,736,748 | 3/1988 | Nakamura et al. . |
| 4,774,955 | 10/1988 | Jones . |
| 4,775,514 | 10/1988 | Barnikol et al. ................... 422/68 |
| 4,785,814 | 11/1988 | Kane . |
| 4,786,474 | 11/1988 | Cooper . |
| 4,798,738 | 1/1989 | Yafuso et al. . |
| 4,801,551 | 1/1989 | Byers et al. ....................... 486/133 |
| 4,803,049 | 2/1989 | Hirschfeld et al. ................ 422/58 |
| 4,810,655 | 3/1989 | Khalil et al. . |
| 4,824,789 | 4/1989 | Yafuso et al. ..................... 436/68 |
| 4,830,013 | 5/1989 | Maxwell . |
| 4,833,091 | 5/1989 | Leader et al. ..................... 436/133 |
| 4,849,172 | 7/1989 | Yafuso et al. ..................... 422/55 |
| 4,851,195 | 7/1989 | Matthews .......................... 422/68 |
| 4,886,338 | 12/1989 | Yafuso et al. . |
| 4,919,891 | 4/1990 | Yafuso et al. . |
| 4,925,268 | 5/1990 | Iyer et al. . |
| 4,965,087 | 10/1990 | Wolfbeis et al. . |
| 4,989,606 | 2/1991 | Gehrich et al. ................... 128/637 |
| 4,999,306 | 3/1991 | Yafuso et al. . |
| 5,030,420 | 7/1991 | Bacon et al. . |
| 5,039,492 | 8/1991 | Saaski et al. ..................... 436/138 X |
| 5,081,041 | 1/1992 | Yafuso et al. ..................... 436/68 |

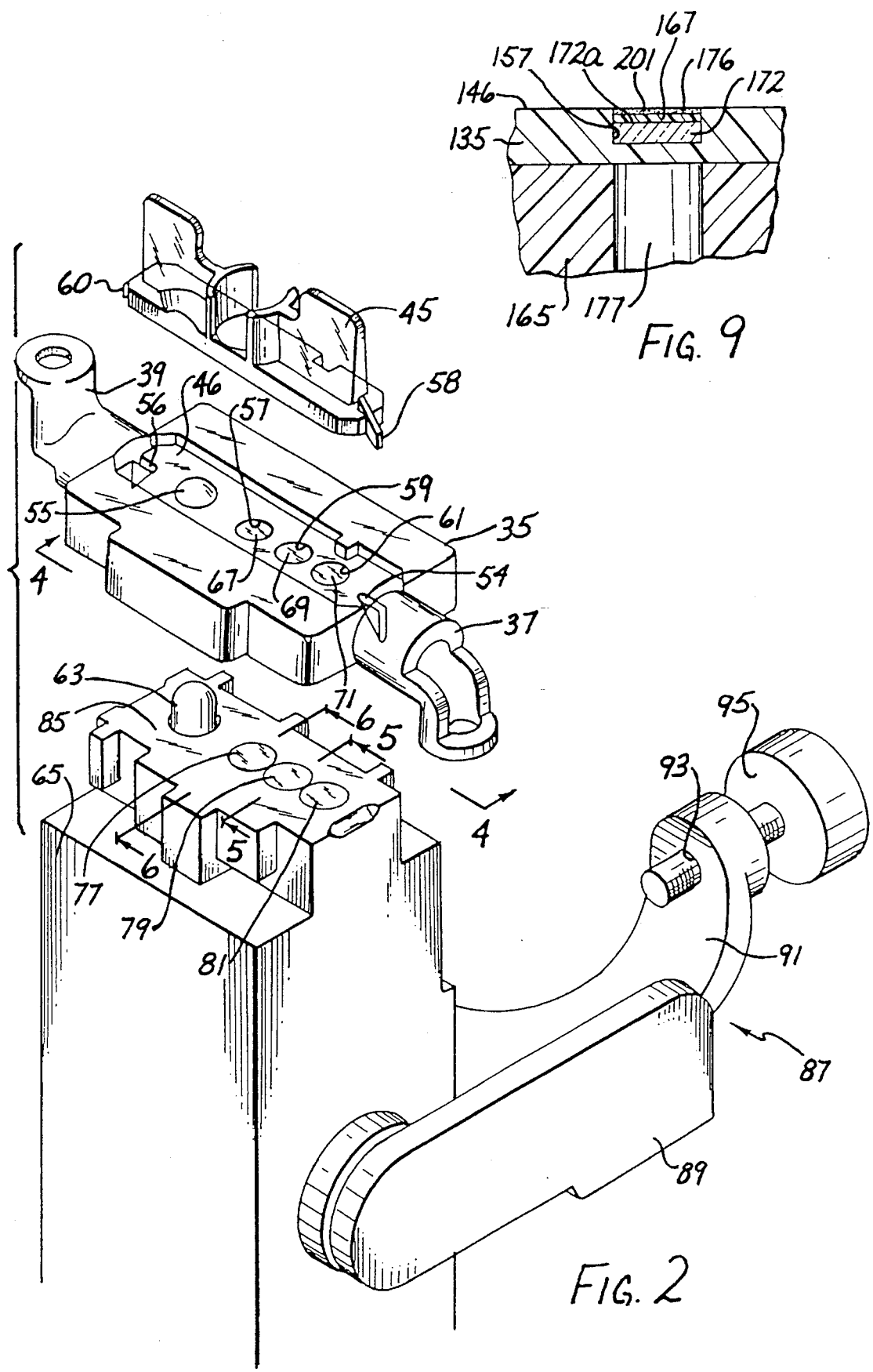

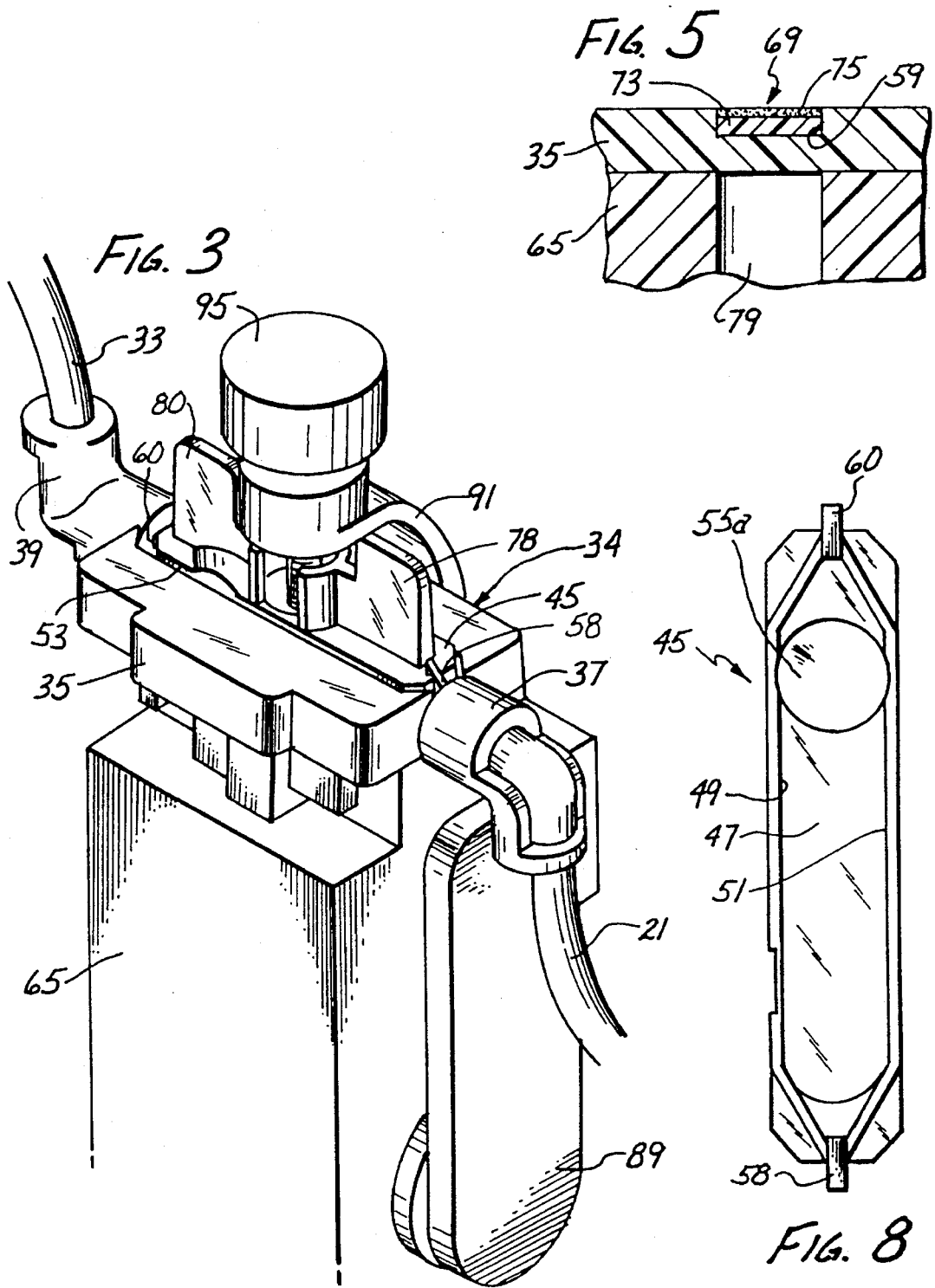

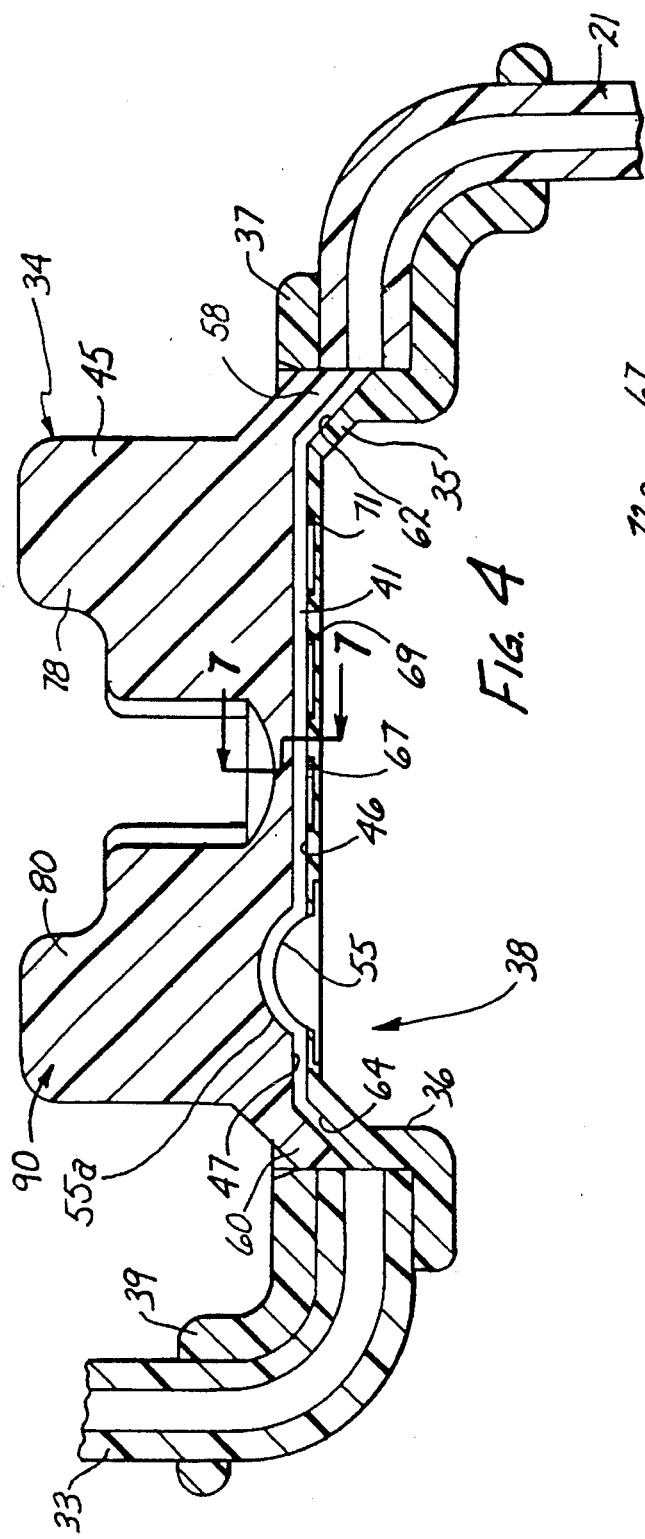
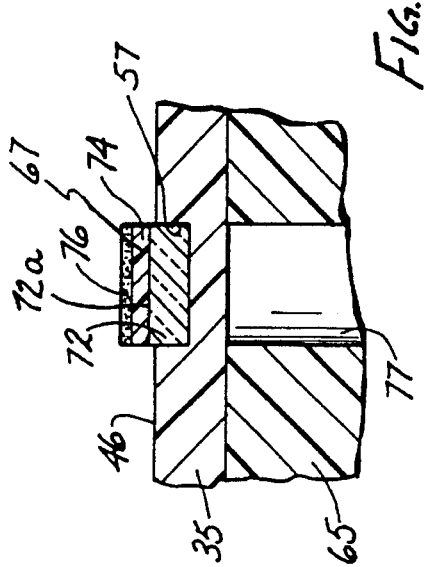
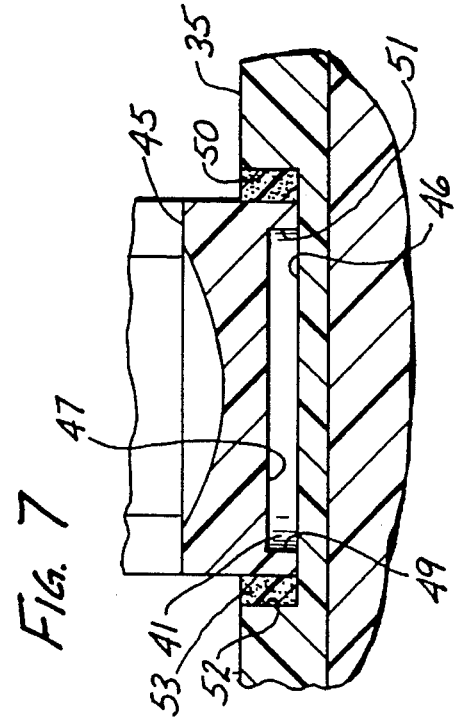

APPARATUS AND METHOD FOR USE IN MEASURING A COMPOSITIONAL PARAMETER OF BLOOD

This application is a continuation of application Ser. No. 07/564,800 filed Aug. 7, 1990, now abandoned entitled *Apparatus and Method for Use in Measuring a Compositional Parameter of Blood* which is a continuation-in-part of application Ser. No. 229,617 filed Aug. 8, 1988 now U.S. Pat. No. 4,989,606 which is a continuation-in-part of application Ser. No. 008,937 filed Jan. 30, 1987 now U.S. Pat. No. 4,830,013.

BACKGROUND OF THE INVENTION

It is often necessary or desirable to measure various compositional parameters of blood, such as the presence and/or concentration of blood constituents, such as blood gases, hydrogen ions (pH), electrolytes, glucose, red blood cells and the like. This can be accomplished in real time in an extracorporeal blood loop as described in Cooper U.S. Pat. No. 4,640,820, in vivo as disclosed in Grandparent U.S. Pat. No. 4,830,013, and in a sensor cassette as shown in parent application Ser. No. 229,617. The sensor cassette is located outside the body of the patient and may be attached to, for example, the arm of the patient. One important advantage of the sensor cassette is that only a relatively small amount of blood is needed to obtain accurate and reliable blood analysis.

The sensor cassette may include a housing having a wall defining a passage which is adapted to receive blood. A sensor is mounted on the housing in a position to be contacted by the compositional parameter of the blood in the passage. The sensor provides a signal in response to the compositional parameter of interest which is usable in determining the presence of, or a quantitative measure of, the compositional parameter of interest.

SUMMARY OF THE INVENTION

This invention provides a sensor cassette having improved accuracy in measuring the compositional parameters of blood. This is accomplished utilizing a support element having particular characteristics and employing this support element in a particular manner.

More specifically, it has been found that polycarbonate, the preferred material for the housing, is at least somewhat permeable to oxygen and carbon dioxide. As such, the polycarbonate housing can form, in effect, a sink for these two gases. For example, the polycarbonate can become charged to a degree with oxygen and carbon dioxide from the atmosphere and then release these gases into the oxygen and carbon dioxide sensors. This somewhat permeable nature of the polycarbonate to oxygen and carbon dioxide can reduce the accuracy of the readings obtained for the measurement of these two partial pressures.

One solution to this problem would be to replace the polycarbonate with a material which is not permeable to any of the compositional parameters of blood. However, when the many requirements for the housing are considered, polycarbonate is the preferred material. For example, the housing is disposable and, therefore, should be constructed of relatively inexpensive material which can be readily molded. It should also be autoclavable and be readily adherable to other components. In addition, to enable the use of optical sensors, which are the preferred sensors, it should have optical clarity at the wavelengths of interest. When considering these requirements, polycarbonate is the material of choice for the housing.

Accordingly, the present invention employs a support element which is less permeable to oxygen and carbon dioxide than is polycarbonate. This support element is carried by a region of the wall of the passage through the housing, and the sensor is, in turn, carried by the support element. The support element separates the sensor from at least a portion of the wall so that the effect of the permeability of the housing to the compositional parameters of blood on the signal from the sensor is reduced. In the case of oxygen and carbon dioxide, this means that the signals from the sensors more accurately represent the partial pressures or concentrations of these gases. In a broader sense, the sensor provides a signal in response to the compositional parameter of interest which is usable in determining the presence of, or a quantitative measure of, the compositional parameter of interest.

The present invention reduces, and preferably minimizes or eliminates, direct contact between the housing and the sensor. Consequently, direct interchange of oxygen and carbon dioxide between the sensor and the housing is correspondingly reduced, minimized or eliminated.

In a broader sense, this invention enables the wall of the housing which defines the passage to be at least somewhat permeable to any compositional parameter of blood and correspondingly provides a support element which is less permeable to that compositional parameter than the housing. Accordingly, in a broader sense, the invention is not limited to a polycarbonate housing and oxygen and carbon dioxide but is applicable to providing a support element that is less permeable to the compositional parameter of blood than is the housing. Thus, the housing may be constructed of various polymeric materials and ceramics.

The support element is preferably, although not necessarily, in a cavity in a region of the wall of the housing. To maintain the integrity of the housing and to facilitate assembly, the cavity preferably does not extend all the way through the wall. The cavity provides several advantages, including a convenient recess in which to mount the support element, and it reduces the extent to which, if any, the support element and sensor project into the passage of the housing.

In one embodiment, the support element projects out of the cavity and terminates in a support surface which is also outside the cavity, and the sensor is on the support surface. This construction has the advantage of completely physically separating the sensor from direct contact with any part of the wall. It also is somewhat easier to make in the small sizes which are preferably employed with the sensor cassette.

In another embodiment, the sensor and support element are completely received within the cavity. In addition, if a gas permeable overcoat is provided on the sensor, it also is entirely received within the cavity. In this embodiment, the overcoat is preferably substantially flush with the wall surrounding the cavity. This construction has the advantage of providing no projection into the passage as a result of employing the sensor-support element construction and thereby provides a smooth passage for blood flow.

The support element can be constructed of any material which is less permeable than the housing to the compositional parameter of interest. In addition, if an optical sensor is employed, the support element should be transparent at the wavelengths of interest. A preferred material for the support element is glass in that it has the desired transparency and is essentially impermeable to all blood compositional parameters. Other materials which meet these requirements can be used, if desired.

Preferably, the optical sensor is fluorescent. However, other optical sensors, as well as non-optical sensors, such as electrochemical sensors, can be employed, if desired.

The present invention has its greatest utility where the blood volume at the sensor is relatively small. In the case of the passage in the housing being a flow-through passage, the invention has its greatest utility where the blood flow rate is relatively small. For example, for relatively high blood flow rates, such as exist in extracorporeal systems where the blood flow rate may be about 3 liters per minute, the effect of a somewhat permeable housing has only a negligible affect on the compositional parameters of the blood. However, for flow rates no greater than about 3 cubic centimeters per hour, the present invention has great utility in improving the accuracy of the measurements of the compositional blood parameters.

This "physical separation" concept is particularly useful where the sensing element is used to determine the concentration of a blood gas, such as oxygen and carbon dioxide, and provides for more accurate determinations. Such physical separation is achieved, for example, by locating the sensing element on a support element which itself physically contacts, e.g., is secured to, the housing. This support element, which may be made out of glass and the like materials, is preferably substantially impermeable to blood gases, and preferably is substantially transparent.

The invention, together with additional features and advantages thereof, may best be understood by reference to the following description taken in connection with the accompanying illustrative drawings.

BRIEF DESCRIPTION OF THE DRAWINGS

FIG. 2 is an exploded view, in perspective, of certain components of the embodiment of the present assembly shown in FIG. 1.

FIG. 3 is a perspective view of the components in FIG. 2 shown assembled and ready for use.

FIG. 4 is a cross-sectional view taken along line 4—4 of FIG. 2.

FIG. 5 is a cross-sectional view taken along line 5—5 of FIG. 2.

FIG. 6 is a cross-sectional view taken along line 6—6 of FIG. 2.

FIG. 7 is a cross-sectional view taken along line 7—7 of FIG. 4.

FIG. 8 is a bottom plan view of one of the housing components (the housing top) of the embodiment of the present. assembly shown in FIG. 1.

FIG. 9 is a sectional view similar to FIG. 6 showing another embodiment of the invention.

DETAILED DESCRIPTION OF THE DRAWINGS

Figure 1:
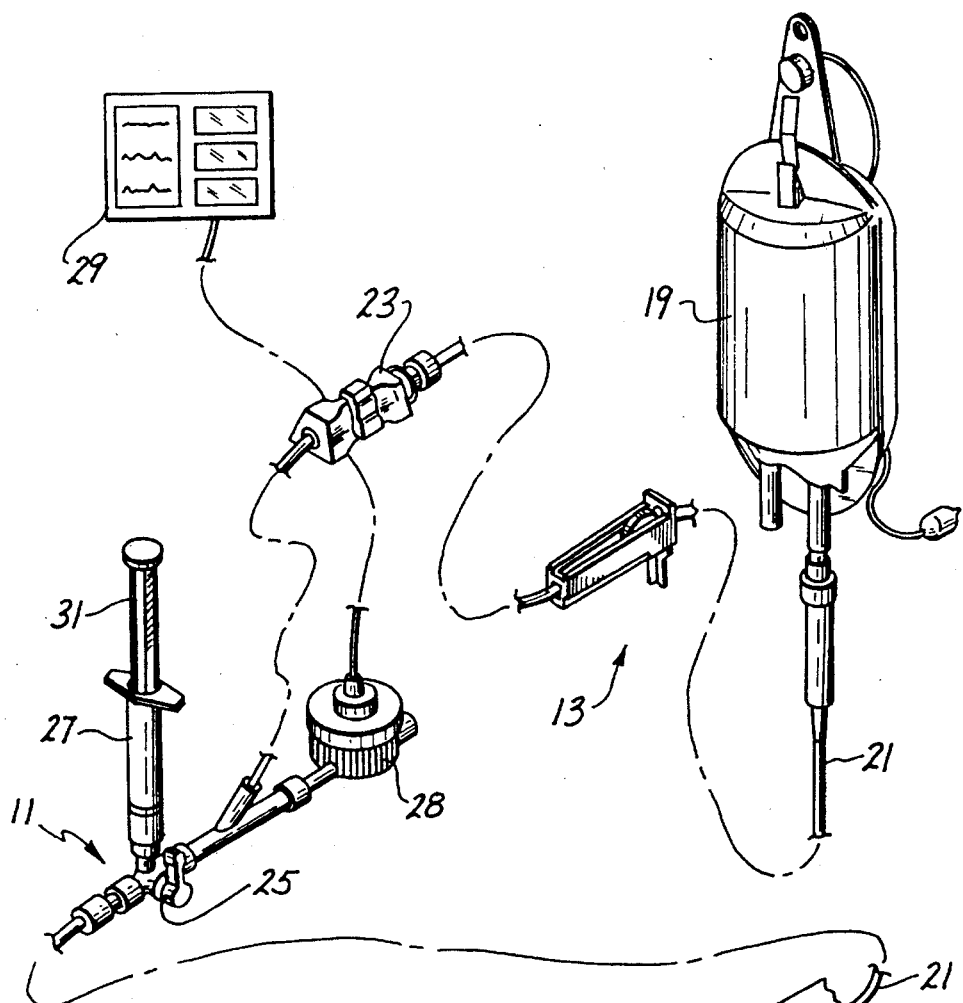
FIG. 1 is a schematic illustration showing one embodiment of the present assembly in use.
Figure 1:
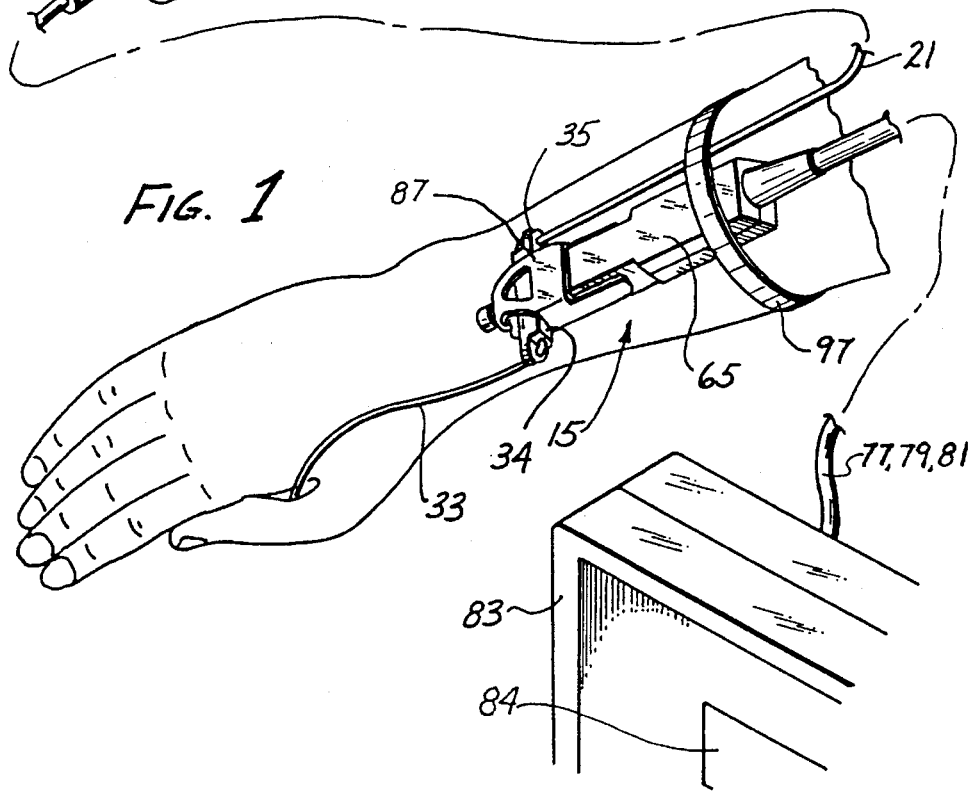

FIG. 1 shows an assembly 11 for the measurement of various blood compositional parameters, and particularly the pH value and the concentrations of oxygen and carbon dioxide of blood. Although the assembly 11 can be of different constructions, in this embodiment it includes a solution introducing system 13 and a sensor assembly 15.

Generally, the solution introducing system 13 introduces an appropriate flush solution, e.g., an anti-clotting solution, such as a heparinized saline solution, through various components of the sensor assembly 15 to the patient to keep the line leading to the patient patent. Although this can be accomplished in different ways, in the embodiment shown schematically in FIG. 1, the system 13 includes a pressurized source 19 of heparinized saline solution, a first conduit 21 leading from the source to the sensor assembly 15, a drip control and rapid flush valve 23, a stopcock 25, a volume oscillator 27, a pressure transducer 28, and a pressure monitor 29. Many of the components of the solution introducing system 13 may be conventional, and this system may include other components, if desired.

In the illustrated embodiment, solution from the pressurized source 19 flows through the valve 23 at a relatively slow rate, such as 2 to 5 ml/hour. The solution flows through the first conduit 21, past the volume oscillator 27, through various components of the sensor assembly 15 to the patient. If a more rapid flow rate from the source 19 is desired, as for example during priming, the valve 23 can be manually opened to provide a relatively high solution flow rate.

volume oscillator 27 may have any one of a number of different structures and configurations. The embodiment illustrated is a cylinder/piston type syringe which is capable of drawing a vacuum in first conduit 21 by manually moving piston 31 away from stopcock 25. This vacuum can be released by manually moving piston 31 toward stopcock 25. There is no net or average flow or pumping of blood in either direction as a result of reciprocation of the plunger 31.

Stopcock 25 can be manipulated into position (1) in which volume oscillator 27 is effectively out of the system or position (2) in which the volume oscillator 27 is in direct fluid communication with that part of first conduit 21 downstream (based on the general direction of flow of the flush fluid from source 19) from stopcock 25, and that part of first conduit 21 upstream from stopcock 25 is isolated from the remainder of the solution introducing system 13.

The pressure transducer 28 communicates with the first conduit 21 and can measure the pressure therein. Accordingly, with the second conduit 33 in fluid communication with the vascular system of a patient, the pressure transducer 28 can provide blood pressure readings. By placing stopcock 25 in position (1), the volume oscillator 27 does not affect the blood pressure readings provided by the transducer 28.

FIGS. 2 to 8 show various components of the sensor assembly 15. A sensor cassette 34 is located between first conduit 21 and second conduit 33. The sensor cassette includes a housing base 35 and a housing top 45. The housing base 35 includes a first tubing fitting 37, which is secured directly to first conduit 21, and a second tubing fitting 39, which is secured directly to second conduit 33. A fluid passage 41 is located between housing base 35 and housing top 45. The housing base 35 and the housing top 45 cooperate to form a housing 90 (FIG. 4). As shown in FIGS. 1–4, the first and second tubing fittings 37 and 39 are configured so that tubing retention sections thereof and the first and second conduits 21 and 33 are oriented (out of housing base 35) in mutually opposing, coplanar directions perpendicular to the general directions of flow through fluid passage 41. As can be seen in FIG. 1, these mutually opposing directions are generally parallel to the surface of the patient's arm on which sensor assembly 15 is located. Housing base 35 includes a first recess which is defined by bottom wall 46 and first recess sidewall 50 and second recess sidewall 52. Housing top 45 includes a second recess which is defined by top wall 47, first sidewall 49 and second side wall 51. The fluid passage 41 is formed by placing housing top 45 in contact with bottom wall 46 of housing base 35, as best shown in FIG. 7. The fluid passage 41 is defined by an internal wall of the housing 90, such wall including the walls 46, 47, 49 and 51. An adhesive 53 is placed in the substantially annular space formed between housing top 45 and housing base 35. The bottom wall 46, top wall 47, first sidewall 49 and second sidewall 51 define fluid passage 41.

An edge 36 extends around the underside periphery of housing base 35 and forms a recess 38.

Housing base 35 includes a first hole 54 and a second hole 56 which are in fluid communication with first tubing fitting 37 and second tubing fitting 39, respectively. Housing top 45 includes a first tab 58 and a second tab 60 which fit into first and second holes 54 and 56, respectively, to form first and second channels 62 and 64. These channels 62 and 64 provide flow paths for blood from first and second conduits 21 and 33, respectively, and form end portions of the fluid passage 41.

Fluid passage 41 has a cross-sectional area which is about 1.3 times the largest cross-sectional area available for fluid flow of either first conduit 21 or second conduit 33. Also, the distance between the first sidewall 49 and the second sidewall 51 of fluid passage 41 as shown in FIG. 7 is about 11.6 times the shortest distance between the top wall 47 and the bottom wall 46 of fluid passage 41.

The bottom wall 46 of fluid passage 41 includes a raised area 55 and three (3) circular cavities or indents 57, 59 and 61 which, as shown in FIG. 4, do not extend through the wall 46. Top wall 47 of housing top 45 includes a corresponding raised area 55a. The raised areas 55 and 55a are adapted to receive the distal end of the thermistor 63 which is located on the transmission block 65. During normal use, housing base 35 is held in close proximity to transmission block 65 so that the distal end of thermistor 63 extends into raised area 55. In this position, thermistor 63 is able to provide an accurate reading of the temperature of the blood in fluid passage 41.

The sensor cassette 34 also includes sensors 67, 69 and 71. Each of the indents 57, 59 and 61 is associated with a different one of sensors 67, 69 and 71, respectively. In this embodiment, each of the sensors 67, 69 and 71 includes a different fluorescent optical indicator. The indicators in sensors 67, 69 end 71 respond to the concentration of carbon dioxide, the pH and the concentration of oxygen, respectively, in the patient's blood to provide optical signals indicative of the compositional parameter sensed.

In general, sensors 67, 69 and 71 can be structured so that the optical indicator is incorporated or combined with a matrix material, e.g., a polymer matrix material. In particular, sensor 69 is structured as shown in FIG. 5. Sensor 69 includes an optical indicator sensitive to the pH of blood embedded in a hydrophilic polymer 73 which is placed in indent 59. Hydrophilic polymer 73 is permeable to the component, hydrogen ions, in the blood to be sensed. An opaque overcoat 75 is placed on top of polymer 73 and serves to optically isolate sensor 69 from the external environment. Overcoat 75 is permeable to the component to be sensed.

FIG. 6 illustrates the structure of sensor 67. It should be understood that sensor 71 is structured similarly to sensor 67. A support element in the form of a glass disc or support element 72 is substantially transparent or optically clear to the signals sent to, and transmitted by, sensor 67 and is sized to fit into cavity 57 and to extend a slight distance above the bottom wall 46 of fluid passage 41. Sensor 67 includes a polymer 74 and an optical indicator sensitive to the concentration of carbon dioxide in blood. Polymer 74 is permeable to the compositional parameter, carbon dioxide, in the blood to be sensed. As seen in FIG. 6, the glass disc 72 physically separates the sensor 67 from the housing base 35. An opaque overcoat 76 is placed on top of sensor 67 and serves to optically isolate the sensor 67 from the external environment. Overcoat 76 is permeable to the component to be sensed. The glass disc 72 is then placed in recess 57 and secured, e.g., adhesively secured, in place. This structure is preferred for carbon dioxide sensor 67 and oxygen sensor 71 since hydrophilic polymer 74 and overcoat 76 are physically separated from housing base 35 so that interference from housing base 35 is reduced and more accurate concentration determinations are often obtained. In addition, such structure is relatively easy to manufacture.

As shown in FIG. 6, the glass disc 72 is carried by the region of the bottom wall 46 which defines the cavity 57. The glass disc 72 projects out of the cavity 57 and terminates in a support surface 72a which is outside the cavity 57. The sensor 67 is carried on, and attached to, the support surface 72a, and the overcoat 76 overlies the sensor 67. The sensor 67 is out of contact with the wall 46, and it and the overcoat 76 project into the passage 41.

FIG. 9 shows an alternate embodiment which is identical to the embodiment of FIG. 6 in all respects not shown or described herein. Portions of the embodiment of FIG. 9 corresponding to portions of the embodiment of FIG. 6 are designated by corresponding reference characters preceded by the numeral "1".

The only difference between the embodiments of FIGS. 6 and 9 is that, in the latter, the sensor 167 and the overcoat 176 are both received within the cavity 157. More specifically, the glass disc 172 terminates outwardly in a support surface 172a which is inside the cavity 157. The overcoat terminates in an outer surface 201 which is substantially flush with the wall 146.

In the embodiment of FIG. 9, the glass disc 172 physically separates the sensor 167 from essentially all direct contact with the housing base 135. There is, however, direct contact between the periphery of the sensor 167 and the housing base 135. In FIG. 6, this peripheral contact, as well as all other contact, between the sensor 67 and the housing base 35 is completely avoided. The embodiment of FIG. 9 can be employed in the sensor cassette of FIG. 4 for either or both of the oxygen or carbon dioxide sensors.

In addition to thermistor 63, transmission block 65 carries optical fibers 77, 79 and 81, which are designed and structured to excite, and transmit signals from, sensors 67, 69 and 71, respectively. Fibers 77, 79 and 81 transmit signals from sensors 67, 69 and 71, respectively, to an instrument 83 which includes a display module 84. Instrument 83 processes the signals from sensors 67, 69 and 71 and provides a display of the current carbon dioxide concentration, pH and oxygen concentration of the patient's blood.

Housing top 45 includes two outwardly extending wings 78 and 80 which are useful to effectively hold housing top 45 during manufacture of the housing. In addition, wings 78 and 80 perform a useful function during use of the sensor assembly 15. Thus, wings 78 and 80 act as heat insulators to reduce the temperature variation of blood in the fluid passage 41. Maintaining relatively constant temperature in fluid passage 41 allows one to more accurately measure the compositional parameter or parameters of interest. This "heat insulator" feature is particularly applicable where the housing top 45 is made of a heat insulating material, e.g., a polymeric material. If desired, transmission block 65 may provide heat to aid in maintaining the temperature in fluid passage 41.

Housing base 35 may be made of the same or different material relative to housing top 45. However, it is important that at least a portion of housing base 35 be transparent to the light signals being sent and received by transmission block 65.

Preferably, the housing 90 is constructed of a transparent polymeric material. More preferably, the polymeric material is polycarbonate. Polycarbonate is somewhat permeable to both oxygen and carbon dioxide, whereas the glass disc 72 is less permeable (essentially nonpermeable) to oxygen and carbon dioxide than the housing 90.

In use, housing base 35 is fitted onto the distal end 85 of transmission block 65. Distal end 85 is uniquely shaped, and recess 38 is correspondingly shaped so that distal end 85 is received by, and fitted into, recess 38 in a manner to insure proper alignment between optical fibers 77, 79 and 81 and sensors 67, 69 and 71, respectively. Such alignment is illustrated in FIGS. 5 and 6. Housing base 35 is held in place on the distal end 85 of transmission block 65 by a movable securement assembly shown generally at 87. Assembly 87 includes two (2) swingable arms 89 attached to either side of transmission block 65. A securement member 91, which extends outwardly from arms 89, includes a threaded hole 93 which is located directly about housing top 45 when arms 89 are in the upright position, as shown in FIG. 3.

A threaded screw 95 is provided and includes threads which matingly engage the threads of threaded hole 93. With housing base 35 in place on distal end 85 of transmission block 65 and arms 89 in the upright position threaded screw 95 can be threaded through threaded hole 93 and made to impact housing top 45. with screw 95 contacting housing top 45, housing base 35 is secured in place in proper relation to transmission block 65. When it is desired to remove housing base 35 from transmission block 65, screw 95 is simply threaded back up hole 93, and arms 89 are swung down from the upright position. The housing base 35 is then free to be removed from the transmission block 65.

Transmission block 65 is of such a size that it can be easily and conveniently "worn" on the arm of the patient whose blood is being analyzed, as shown in FIG. 1. This feature reduces the amount of blood which is withdrawn from the patient, and also reduces the distance the blood must traverse along tube 33 in order to get the desired analyses. The transmission block 65 may be secured to the patient by means of strip 97, which is made up of hook and loop fasteners, e.g., velcro fasteners. Of course, other means, e.g., conventional means, may be employed to removably secure transmission block 65 to the patient.

Assembly 11 functions as follows. During "normal" operation, stopcock 25 is in position (1) and a supply of flush solution from source 19 is passed through first conduit 21, flow passage 41 and second conduit 33 into the patient. Using this configuration the blood pressure of the patient can be monitored. when it is desired to chemically analyze the patient's blood, stopcock 25 is placed in position (2).

Piston 31 is then lifted away from stopcock 25. This creates a vacuum in first conduit 21 and second conduit 33 which, in turn, causes blood, from the patient, to flow through second conduit 33 into fluid passage 41 and part way into first conduit 21. At this point, optical fibers 77, 79 and 81 are activated so that signals in response to the carbon dioxide concentration, the pH and the oxygen concentration of the blood in fluid passage 41 can be obtained from sensors 67, 69 and 71, respectively.

After these signals have been transmitted for a satisfactory period of time to instrument 83, piston 31 is moved toward stopcock 25, thereby creating a positive pressure in first conduit 21 to urge the blood in first conduit 21, fluid passage 41 and second conduit 33 back into the patient. After the blood has been returned, stopcock 25 is returned to position (1), and flush fluid from source 19 is allowed to flow through first conduit 21, flow passage 41 and second conduit 33 into the patient. Substantially all of the blood in fluid passage 41 is returned to the patient so that no blood coagulation or other buildup is apparent. This feature is important since it allows the patient's blood to be repeatedly analyzed with reliable and reproducible accuracy without creating conditions, e.g., blood clotting, which might harm the patient.

The transparency of the housing base allows the signals from the sensors 67, 69 and 71 to be readily communicated to optical fibers 77, 79 and 81, respectively. In addition, housing base 35 and housing top 45 are each made of materials which are substantially impermeable to the liquid blood in fluid passage 41. This feature effectively isolates transmission block 65 from exposure to the patients blood.

When blood is in the passage 41, the glass disc 72 isolates the associated sensors 67 and 71 from the housing base 35 and the wall 46. Preferably, with either of the embodiments of FIG. 6 or FIG. 9, the effect of the permeability of the housing 35 on the oxygen and carbon dioxide signals from the sensors 67 and 71 is substantially eliminated. This is true even though the housing base 35 is constructed of polycarbonate and serves as a sink for oxygen and carbon dioxide in the external environment. Consequently, the accuracy of the oxygen and carbon dioxide partial pressure readings is improved.

With this invention, only very small quantities of blood are drawn into and through the passage 41. For example, 0.1 to about 0.2 cubic centimeters of blood will pass through the passage 41 during any one measurement time. Of course, this invention is applicable even though greater or lesser quantities of blood pass through the passage 41 during a measurement time. Nevertheless, the compositional parameters of interest are sensed with the sensors 67, 69 and 71 with very good accuracy even though the housing 90 is constructed of polycarbonate which is permeable to oxygen and carbon dioxide.

After use, the securement assembly 87 is released, thereby allowing the housing base 35 to be removed from the distal end 85 of transmission block 65. The components of assembly 11 which have been exposed to the patient's blood, e.g., second conduit 33, housing base 35, housing top 45 and first conduit 21, are preferably disposed of. Transmission block 65 and instrument 83, which have not been exposed to the patient's blood, can be reused repeatedly. This feature represents a substantial advantage for the present system. Thus, the relatively inexpensive components of the sensor assembly 15 can be economically discarded after a single use, e.g., use by a single patient. The much more expensive components of the blood so that they are not exposed to such blood and are available for repeated reuse without danger of cross-patient blood contamination.

Although exemplary embodiments of the invention have been shown or described, many changes, modifications and substitutions may Re made by one having ordinary skill in the art without necessarily departing from the spirit and scope of this invention.

We claim:

1. A sensor cassette for use in measuring a compositional parameter of blood comprising:

a housing having a wall defining a passage which is adapted to receive blood, said wall being at least somewhat permeable to the compositional parameter of blood;

a support element carried by a region of said wall;

said support element being less permeable to the compositional parameter of blood than said housing;

a sensor carried by the support element, said sensor providing a signal in response to the compositional parameter of blood; and said support element separating the sensor from at least a portion of said region of the wall whereby the effect of the permeability of the housing to the compositional parameter of blood on said signal is reduced.

2. A sensor cassette as defined in claim 1 wherein said wall includes polymeric material which is at least somewhat permeable to the compositional parameter of blood.

3. A sensor cassette as defined in claim 2 wherein the polymeric material includes polycarbonate, said compositional parameter of blood is blood gas and said sensor provides said signal in response to blood gas.

4. A sensor cassette as defined in claim 1 wherein said compositional parameter of blood is blood gas and said sensor provides said signal in response to the partial pressure of the blood gas.

5. A sensor cassette as defined in claim 2 wherein the polymeric material includes polycarbonate and the support element is constructed of glass.

6. A sensor cassette as defined in claim 1 wherein said wall has a cavity therein and the support element is in said cavity.

7. A sensor cassette as defined in claim 6 wherein the support element terminates outwardly in a support surface and the sensor is carried on the support surface.

8. A sensor cassette as defined in claim 7 wherein the support surface is outside the cavity.

9. A sensor cassette as defined in claim 7 including a gas permeable overcoat on the sensor, said sensor and overcoat being received in the cavity.

10. A sensor cassette for use in measuring blood gas of blood from a patient comprising:

a housing of polymeric material having a wall defining a passage, said passage being adapted to receive blood;

a support element carried by a region of said wall;

said support element being substantially impermeable to blood gases; and a sensor carried by the support element and physically separated from said region of said wall by said support element, said sensor being in a position to be contacted by blood gas from blood which is received in the passage, said sensor providing a signal in response to the concentration of blood gas.

11. A sensor cassette as defined in claim 10 wherein said wall has a cavity therein and the support element is in said cavity.

12. A sensor cassette as defined in claim 11 wherein the support element projects out of the cavity and terminates in a support surface which is outside the cavity and said sensor is on said support surface.

13. A sensor cassette as defined in claim 10 wherein the sensor is an optical sensor and the support element is substantially transparent.

14. A sensor cassette as defined in claim 10 wherein the support element is constructed of glass.

15. A sensor cassette for use in measuring blood gas of blood from a patient comprising:

a housing having a wall of polymeric material defining a passage, said passage being adapted to receive blood;

said wall having a cavity opening into said passage;

a support element in said cavity which is less permeable to blood gas than the polymeric material, said support element terminating outwardly in a support surface; and a sensor carried by the support element on said support surface, said sensor being capable of providing a signal in response to the concentration of the blood gas.

16. A sensor cassette as defined in claim 15 wherein the support element is constructed of glass.

17. A sensor cassette as defined in claim 16 including a gas permeable overcoat on the sensor.

18. A sensor cassette as defined in claim 17 wherein the support surface is outside of the cavity and the sensor is a fluorescent sensor.

19. A sensor cassette as defined in claim 15 wherein the cavity does not extend all the way through said wall.

20. A sensor cassette for use in measuring blood gas of blood from a patient comprising:

a housing having a wall of a transparent polycarbonate material defining a passage, said passage being adapted to receive blood;

said wall having a cavity which does not extend all the way through the wall, said cavity opening into said passage;

a support element in said cavity which is less permeable to blood gas than the wall of polycarbonate material, said support element terminating outwardly in a support surface; and a fluorescent sensor carried by the support element on said support surface, said sensor being capable of providing a fluorescent signal in response to the concentration of blend gas, and the support element being transparent to said fluorescent signal.

* * * * *

UNITED STATES PATENT AND TRADEMARK OFFICE
CERTIFICATE OF CORRECTION

PATENT NO. : 5,462,052
DATED : October 31, 1995
INVENTOR(S) : Gehrich et al

It is certified that error appears in the above-indentified patent and that said Letters Patent is hereby corrected as shown below:

Column 3, line 56; delete "present." and insert in place thereof --present--.

Column 4, line 23; delete "volume" and insert in place thereof --Volume--.

Column 7, line 35; delete "with" and insert in place thereof --With--.

Column 8, line 60; delete the words "of the blood so that they".

Column 8, line 65; delete "Re" and insert in place thereof --be--.

Column 10, line 52; delete "blend" and insert in place thereof ---blood---.

Signed and Sealed this

Thirteenth Day of August, 1996

Attest:

BRUCE LEHMAN

Attesting Officer    Commissioner of Patents and Trademarks